US010251608B2

(12) United States Patent
Galasso

(10) Patent No.: US 10,251,608 B2
(45) Date of Patent: Apr. 9, 2019

(54) SYSTEM AND METHOD FOR DETECTING BAROPOSTURAL PARAMETERS

(71) Applicant: BARO POSTURAL INSTRUMENTS SRL, Rome (IT)

(72) Inventor: Francesco Galasso, Rome (IT)

(73) Assignee: BARO POSTURAL INSTRUMENTS SRL, Rome (RM) (IT)

( * ) Notice: Subject to any disclaimer, the term of this patent is extended or adjusted under 35 U.S.C. 154(b) by 646 days.

(21) Appl. No.: 14/893,988

(22) PCT Filed: Apr. 16, 2014

(86) PCT No.: PCT/IB2014/060768
§ 371 (c)(1),
(2) Date: Nov. 25, 2015

(87) PCT Pub. No.: WO2014/191849
PCT Pub. Date: Dec. 4, 2014

(65) Prior Publication Data
US 2016/0113584 A1    Apr. 28, 2016

(30) Foreign Application Priority Data

May 30, 2013    (IT) .............................. MI2013A0886

(51) Int. Cl.
*A61B 5/00* (2006.01)
*A61B 5/103* (2006.01)
(Continued)

(52) U.S. Cl.
CPC .............. *A61B 5/706* (2013.01); *A43D 1/025* (2013.01); *A61B 5/0077* (2013.01);
(Continued)

(58) Field of Classification Search
CPC ....... A61B 5/11; A61B 5/1116; A61B 5/1123; A61B 5/706; A61B 5/0077; A61B 5/1036
See application file for complete search history.

(56) References Cited

U.S. PATENT DOCUMENTS 5,271,416 A * 12/1993 Lepley ................. A61B 5/1036
482/120
5,790,256 A    8/1998 Brown et al.
(Continued)

OTHER PUBLICATIONS

PCT International Search Report dated Aug. 14, 2014 for Intl. App. No. PCT/IB2014/060768, from which the instant application is based, 3 pgs.

*Primary Examiner* — Max Hindenburg
(74) *Attorney, Agent, or Firm* — Fredrikson & Byron, P.A.

(57) ABSTRACT

A system (10) for detecting and displaying baropostural parameters comprises a platform (11) with a footplate (15) intended to accommodate a person standing on it and provided with sensors for detecting the pressure distribution of the imprint of the two feet on the footplate. An electronic acquisition device (32) is connected to the sensors for digital acquisition of the pressure distribution in order to create a map of the pressure points of the feet on the footplate. Calculation means (33a) are designed to calculate, for each foot and for both feet on the footplate, the geometric centers (52, 53, 54) and the barycenters (55, 56, 57) of the map of the pressures and display means (33b) display on a screen (31) a graphical representation of the imprints of the two feet on the footplate together with the corresponding geometric centers (52, 53, 54) and barycenters (55, 56, 57) calculated by the calculation means. The footplate may have a rear part (15) which can be raised for simulating shoe heels underneath the heels. Front and/or lateral telecameras (19, 20) may be provided in order to provide further postural data.

18 Claims, 8 Drawing Sheets

(51) Int. Cl.
    *A61B 5/107*          (2006.01)
    *A61B 5/11*           (2006.01)
    *A43D 1/02*          (2006.01)

(52) U.S. Cl.
    CPC .......... *A61B 5/1036* (2013.01); *A61B 5/1072* (2013.01); *A61B 5/1074* (2013.01); *A61B 5/1121* (2013.01); *A61B 5/4561* (2013.01); *A61B 5/743* (2013.01); *A61B 2562/0252* (2013.01)

(56) References Cited

U.S. PATENT DOCUMENTS

| | | | | |
|---|---|---|---|---|
| 6,063,046 | A * | 5/2000 | Allum | A61B 5/1036 600/595 |
| 6,231,527 | B1 * | 5/2001 | Sol | A61B 5/1038 348/143 |
| 7,854,071 | B2 * | 12/2010 | Goonetilleke | A43D 1/02 33/3 R |
| 9,202,386 | B2 * | 12/2015 | Yuasa | A61B 5/1036 |
| 9,955,900 | B2 * | 5/2018 | O'Connor | A61B 5/0064 |
| 2005/0182341 | A1 | 8/2005 | Katayama et al. | |
| 2009/0247909 | A1 | 10/2009 | Mukumoto | |

* cited by examiner

SYSTEM AND METHOD FOR DETECTING BAROPOSTURAL PARAMETERS

RELATED APPLICATIONS

This application is a 35 U.S.C. 371 national stage filing from International Application No. PCT/IB2014/060768, filed Apr. 16, 2014, which claims priority to Italian Application No. MI2013A000886, filed May 30, 2013, the teachings of which are incorporated herein by reference.

FIELD OF THE INVENTION

The present invention relates to an innovative system and an innovative method for detecting baropostural parameters.

In particular, the system and the method are suitable for the study and correction of the load distribution on the lower limbs for postural optimization.

For example, owing to its innovative features, the invention provides a method for objective instrumental evaluation of the differences or deviations in the length of a lower limb, more commonly known as "real shortening" and "apparent shortening" or as "anatomical shortening" and "functional discrepancy".

As a result of the invention it is also possible to study and diagnose postural abnormalities or dysmorphisms and pathologies affecting various parts of the body in order to implement the corresponding corrective procedures.

BACKGROUND

In the ideal case of a human being standing in the correct erect position, the vertical line which passes through the centre of gravity of the body should meet the support surface on the ground at a point defined by the intersection, in the support plane, of a segment in the sagittal direction arranged equidistant from the two feet and a segment in the transverse direction which passes about halfway between the tibiotarsal articulation and the metatarso-phalangeal articulation of the two feet. In this condition, the load is equally distributed between the two feet and between the front contact zone and the rear contact zone of the foot.

The postural defects result in displacement of the contact pressure points and the barycentre forwards or backwards and/or to the right or left, such that they move away from their optimum position.

It is therefore useful to be able to define using instruments with a suitable precision both the deviations from the optimal positions and the effects of the postural corrections applied in order to try to reduce the deviations determined.

Attempts at performing measurements using instruments have been made in the prior art, but the results were not regarded as being satisfactory and complete.

Moreover, it is a widespread belief that a difference in the level of the iliac crests is an indication of an different length of the lower limbs. In reality, the difference in level may be caused by an anteversion of an iliac wing which rotates and flexes further forwards than the other wing. The correction by means of raising of the leg which appears to be shorter therefore results only in an apparent correction of the defect, giving rise to various postural complications.

BRIEF SUMMARY OF EMBODIMENTS OF THE INVENTION

The general object of the present invention is to provide a system and a method for suitably detecting of baropostural parameters.

In view of this object the idea which has occurred is to provide, according to the invention, a system for detecting and displaying baropostural parameters, comprising:

a platform with a footplate intended to accommodate a person standing on it and provided with sensors for detecting the pressure distribution of the imprint of the two feet on the footplate;

an electronic acquisition device connected to the sensors for digital acquisition of the pressure distribution in order to create a map of the pressure points of the feet on the footplate;

calculation means designed to calculate, for each foot and for both feet on the footplate, the geometric centres and the barycentres of the map of the pressure points;

display means (33b) which display on a screen (31) a graphical representation of the imprints of the two feet on the footplate together with the corresponding geometric centres and barycentres calculated by the calculation means.

Advantageously, the footplate has at least one rear zone for supporting the heels which can be controllably raised in order to simulate the presence of shoe heels underneath the heel of the foot.

Still according to the invention the idea which has occurred is to provide a method for detecting and displaying baropostural parameters by means of an electronic system, comprising the steps of:

acquiring electronically the pressure distribution of the imprint of the two feet of a person standing on a footplate with a pressure-sensitive surface;

creating a map of the pressure distribution acquired;

calculating, for each foot and for both feet on the footplate, the geometric centres and the barycentres of the map of the pressure points;

displaying on a screen a graphical representation of the imprints of the two feet together with the corresponding geometric centres and barycentres calculated.

Further characteristic features and advantages of the invention will become clear from the description below.

BRIEF DESCRIPTIONS OF DRAWINGS

In order to illustrate more clearly the innovative principles of the present invention and its advantages compared to the prior art, an example of embodiment applying these principles will be described below with the aid of the accompanying drawings. In the drawings.

DETAILED DESCRIPTION OF EMBODIMENTS OF THE INVENTION

Figure 1:
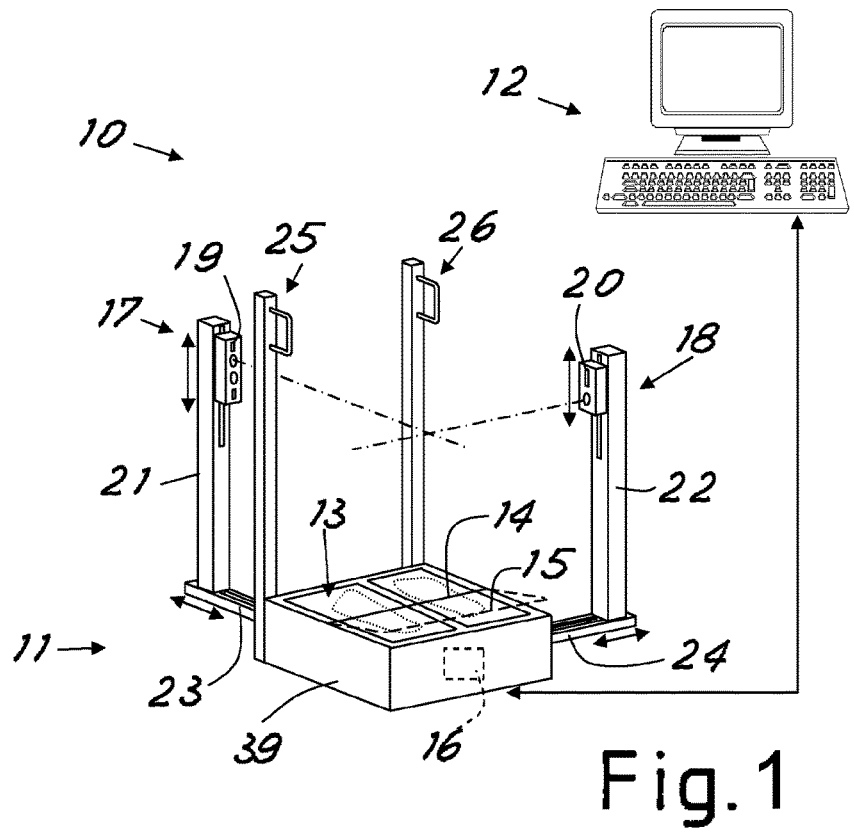
FIG. 1 shows a schematic perspective view of a system for detecting baropostural measurements, provided in accordance with the invention.

With reference to the figures, FIG. 1 shows a system according to the invention, denoted generally by 10, for detecting baropostural parameters, namely parameters suitable for example for determining the correct posture.

The system 10 comprises a detecting platform 11 and an electronic control unit 12. The platform 10 is formed by a base 39 having on its top side a surface or footplate 13 for accommodating a person standing thereon. The footplate or surface 13 has sensors for detecting the pressure distribution on the footplate, which are able to convert this pressure distribution into electric signals, as will be explained below. When a person stands on the footplate with both feet the pressure distribution will be that of the imprint of the two feet made on the footplate itself.

The base may have, for example, a box-like support structure made of aluminium alloy. Transportation handles may also be provided.

The surface with the pressure sensors may be formed with a layer or grid of pressure sensors lined and protected by a resilient layer for supporting the feet, as may be now easily imagined by the person skilled in the art.

Advantageously, the surface 13 is divided along a transverse hinge 14 so as to have at least one rear portion or section 15 thereof which tilts and can be raised, rotating about the hinge 14 by means of a motor-driven actuator 16. This allows the heels of a person standing correctly on the footplate to be raised.

Advantageously, the platform 10 also comprises a front telecamera system 17 and a lateral telecamera system 11 which record, from a front direction and side direction, respectively, a body standing on the surface 13. The main detecting axes of the two telecamera systems are therefore arranged advantageously at right angles in a horizontal plane, as shown schematically in broken lines in FIG. 1.

Preferably, the two telecamera systems each comprise a telecamera group 19, 20 which is movable vertically along a respective column 21, 22 so as to allow heightwise adjustment of the visual field of the telecamera groups, as will be explained below.

Again advantageously, the telecamera groups are also preferably adjustable in terms of horizontal distance from the base 39. This adjustment may be performed preferably by means of sliding of the columns 21 and 22 along corresponding suitable horizontal rails 23 and 24 which are fixed to the base 39 and project from it along the longitudinal and transverse axes of the platform.

The movements of the telecamera groups may be manual or motorized, using systems which may be easily imagined by the person skilled in the art on the basis of the description of the invention provided hitherto.

Advantageously, the platform 10 may comprise two supports 25, 26 which extend upwards from the front corners of the base so that they may be gripped by the hands of a person who stands on the surface 13. These supports, which are preferably provided with suitable gripping handles, may help a person to step up onto and stand correctly on the surface 13.

Figure 2:
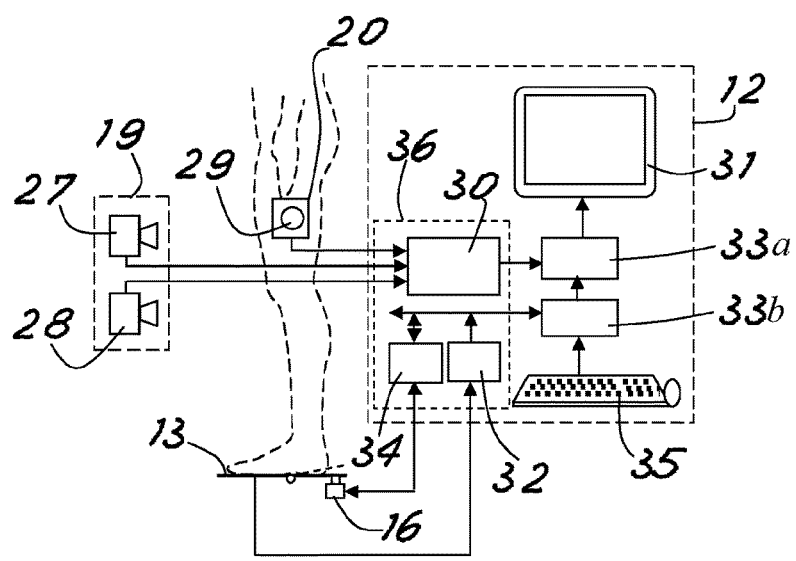
FIG. 2 shows a schematic side elevation and partial view of the system according to FIG. 1.

As can be seen in FIG. 2, the front telecamera group 19 comprises advantageously two telecameras 27, 28, one telecamera for detecting frontally substantially the whole body of a person standing on the surface 13 and the other telecamera for detecting the person from the groin zone to the knee zone. Alternatively, it is also possible to use a single telecamera which allows zooming between these two views by means of a suitable known controllable optical or electronic system, as will be clear to the person skilled in the art.

The lateral group 20 may instead advantageously comprise a single telecamera 29 for laterally detecting substantially the entire body of the person standing on the surface 13. The telecameras may also comprise known illumination means (advantageously of the infrared type) for the detecting zone, such as to allow clear viewing of the desired image of the body being recorded, independently of the surrounding light conditions.

As can be seen again in FIG. 2, the signals of the telecameras are sent to electronic means known per se or an acquisition device 30 of the control unit 12 for converting their electrical image signals into a stream of image data which can be digitally processed, as will become clear below.

The control unit 12 also comprises an electronic means or acquisition unit 32, known per se, which receives electrical signals from the pressure-sensitive surface 13 and converts them into digital signals suitable for processing by a calculation means or unit 33a. These digital signals may for example represent a spatial grid x, y of pressure values on the surface 13. By means of the acquisition device it is possible to create a map of the pressure points of the feet on the footplate.

Advantageously, the control unit 12 also comprises an electronic means or control unit 34 (preferably of the feedback type for suitable accuracy) for the raising actuator 16.

The control unit 12 also has an electronic means or unit 33b for displaying images on the screen 31 and input means or devices 35 which are advantageously formed by a computer keyboard or a pointer device such as a mouse and/or a graphical tablet and/or a touch-sensitive pad and/or an electronic pen or the like. In addition or alternatively, a screen 31 provided with touch-screen functions may also be used.

The calculation and display means 33, the input peripherals and the screen may also advantageously consist of a suitable personal computer suitably programmed and digitally connected to the acquisition and control units 30, 32, 34 via a suitable known interface, as may be easily imagined by the person skilled in the art on the basis of the description of the invention provided here. The units 30, 32, 34 may also be grouped together in a single electronic device 36 connected to the personal computer 31, 33, 35 by means of a single suitable communication channel, for example via a USB interface. The electric circuits which form this device 36 or the individual units may be per se easily imagined by the person skilled in the art on the basis of the description of the invention provided hitherto and will therefore not be further illustrated or described.

The electronic section therefore performs selection of the telecameras and any associated infrared illumination devices, control of the motor for performing raising of the rear part of the footplate, and detecting and storage, where appropriate, of the data output by the pressure sensors associated with the footplate, as well as interfacing with the personal computer for communication of the input and output data.

The pressure-sensitive surface 13 is designed using a technology which is substantially known per se (for example capacitive, load cell resistance and or similar technology) so as to provide data relating to the pressure distribution on the surface with a suitable resolution in both spatial and weight-value terms. For example, the spatial resolution may be of the order of half a centimeter or less and the resolution for measurement of the weight of the order of grams, with a measurement range suitable for the total weight to be detected (for example between 10 and 120 kg).

Suitable pressure sensor devices are per se well-known to person skilled in the art and will therefore not be further described or shown here.

Figure 3:
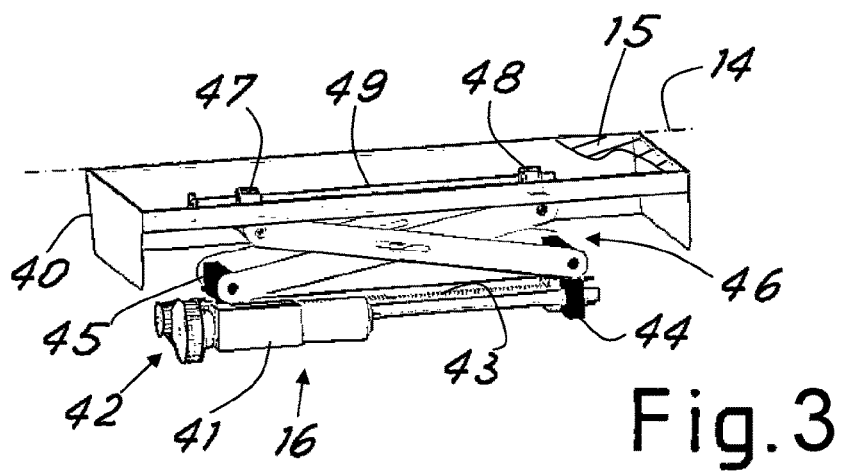
FIGS. 3 and 4 show schematic views of a mechanical detail of the system according to FIG. 1.
Figure 4:
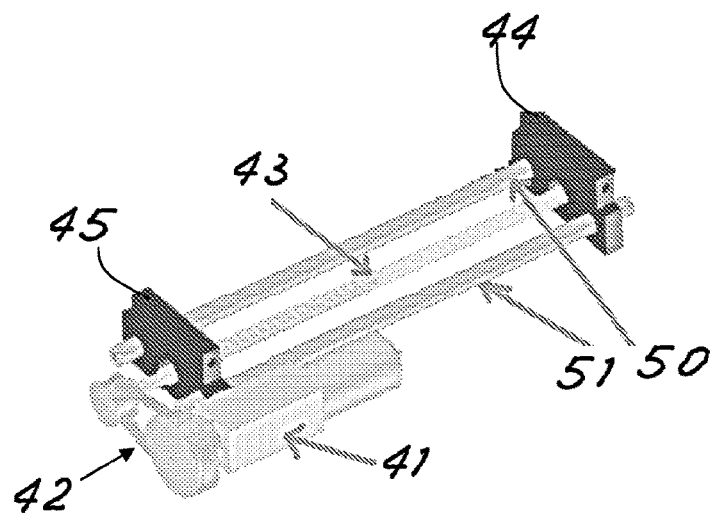

FIGS. 3 and 4 shows a possible advantageous embodiment of the actuator 16 for raising the rear of the footplate. In this embodiment, a frame 40, which supports at the top the surface 15 (for the sake of clarity partially removed in FIG. 3), is hinged on the base along the axis of rotation 14. An electric gearmotor 41 rotates (via a belt drive 42, where appropriate) an actuating screw 43 which causes the displacement, in opposite directions, of two carriages 44, 45. In order to achieve this displacement in opposite directions, the screw may be formed along half its length with a right-handed thread and along its other half with a left-handed thread.

A pantograph structure 46 is attached via its bottom part to the two carriages and at the top is attached to cursors 47, 48 slidable parallel to the axis 14 on a guide 49 which is in turn attached to the frame 40. The connection between cursors and guide is advantageously rotatable about the axis of the guide. A connection between actuator and frame or between frame and base may also be provided such as to allow rotation of the frame about the axis 14 while the pantograph extends or retracts.

As can be clearly seen in FIG. 4 (where the frame 40 and the arms of the pantograph 46 have been removed for greater clarity), the carriages 44, 45 may be advantageously slidable along a pair of parallel guides 50 and 51 arranged on the two sides of the operating screw 43.

It is clear how operation of the motor 41 produces rotation of the surface 15 about the axis 14 with a curved movement having a predetermined maximum amplitude from a horizontal condition of the surface 15.

The gearmotor 41 may also comprise a rotational sensor (not shown), for example an absolute or incremental encoder, for allowing the control unit 34 to perform precise control of the movement, as may be easily imagined by the person skilled in the art.

During use of the system, when a patient stands without shoes on the footplate 13 with their feet slightly apart (as indicated by the foot imprints shown in broken lines in FIG. 1), the pressure-sensitive surface detects the load in the various zones of the foot resting on the surface 13 (also called imprint pressures) and, via the unit 34, communicates the pressure distribution to the calculation device 33a. A map of the pressures is thus created and may also be advantageously shown on the screen 31 as imprint images via the display means 33b.

Advantageously the imprint images may be represented so as to provide a graphical illustration of the pressure distribution of the imprint for each foot.

Figure 5:
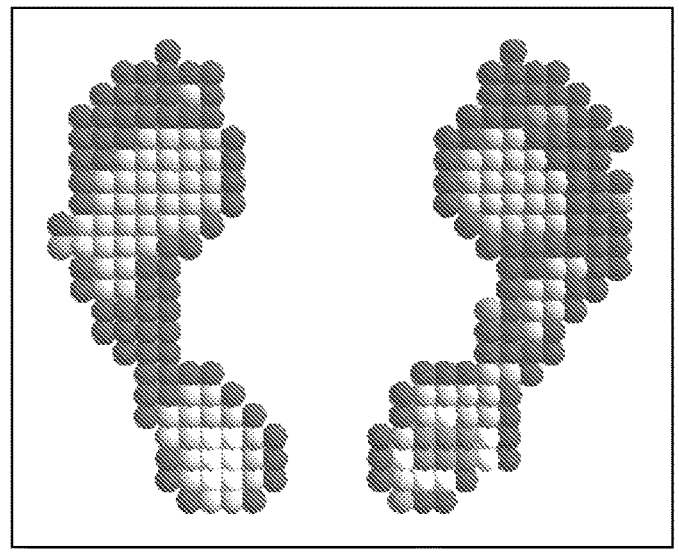
FIGS. 5, 6 and 7 show schematic views of graphical processing screenshots produced by the system according to FIG. 1.

For example FIG. 5 shows a possible representation of the imprint images, where each circle (or sphere) represents a pressure zone which is detected in the corresponding zone of the sensitive surface 13. The degree of pressure may be for example represented by a colour code (advantageously associating a greater pressure with lighter and/or brighter colours) and/or by a numerical value (for example showing a numerical value within each circle or instead of each circle).

If considered useful, the graphical representation may also be different from that shown. For example, it may comprise iso-pressure lines or areas distinguished by colour, solely numerical symbols, etc.

The representation in FIG. 5 in any case indicates in a readily comprehensible manner the distribution of the pressure points on the soles of the two feet.

Using a process which may be easily imagined by the person skilled in the art based also on the description provided here, once the data relating to the distribution of the pressure points of the feet have been acquired, the calculation and display system 33, based on the map of the pressure points, may calculate and trace on the screen 31 the graphical representation of the imprints together with the geometric centres for the contact pressure and the barycentres projected on the support surface, both for the single foot and for the body as a whole. The geometric centres and/or the barycentres may be shown on a displayed image of the pressure map, such as that shown for example in FIG. 5 (FIG. 10 also shows a further example, as will be clarified below) or also on a more schematic image, e.g. of only the contours of the pressure map.

Figure 6:
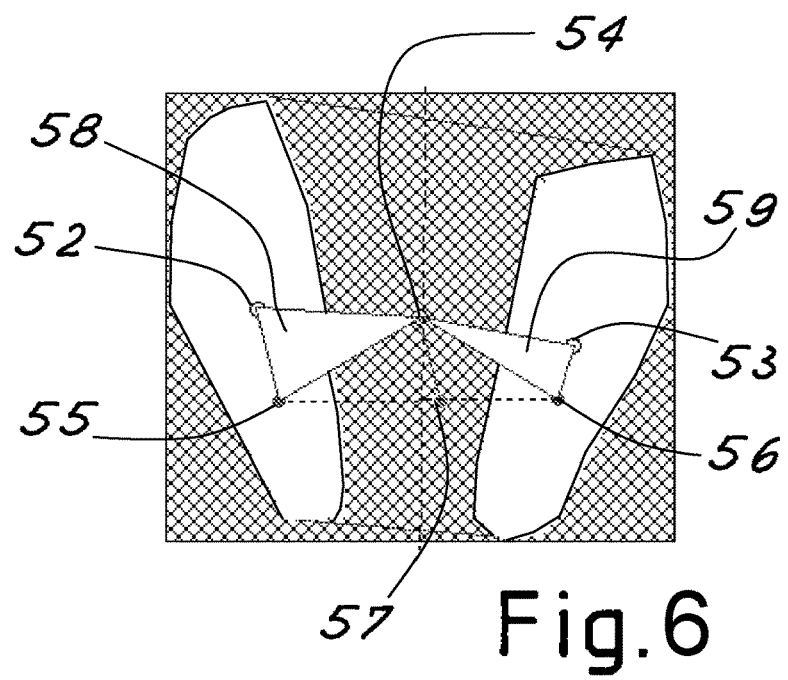

In particular, FIG. 6 shows a possible graphical representation of the result of these calculations, with only the contours of the imprints, which may be easily shown by the system on the screen 31.

This graphical representation shows the outline of the two imprints of the feet and the geometric centres 52, 53 of each foot, the overall geometric centre 54 of the supporting contact and the corresponding barycentres of the contact pressure points for each foot (55, 56) and both feet (57).

Figure 7:
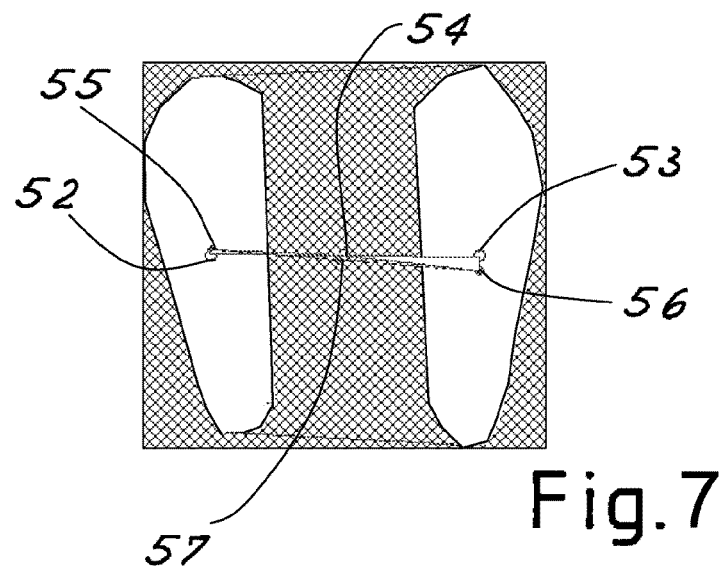

In an ideal posture situation, the geometric centres 52, 53, 54 should substantially coincide with the barycentres 55, 56, 57, as shown for example in FIG. 7.

The greater the difference the more the baropostural condition deviates from the ideal condition.

As shown again in FIGS. 6 and 7, advantageously the calculation and display system 33 indicates two triangles 58, 59 on the imprint picture. These triangles each have vertices which coincide with the overall barycentre, the geometric centre and the barycentre of a foot.

The area and the form of the two triangles provide an immediate representation which varies depending on the degree of postural imbalance overall and of each of the two feet.

The system may thus provide a useful podometric image of the feet without shoes.

As will be further clarified below, if the platform comprises a rear raising mechanism, it is also possible to evaluate immediately the improvement which raised heels of specific height could provide for supporting the foot-soles of the patient.

For example, the image in FIG. 6 could relate to a measurement operation performed with the rear portion of the platform in a horizontal position and coplanar with the front part. This highlights a significant defect in the foot contact pressure of the person being examined.

The image shown in FIG. 7 could instead relate to the same person after the rear part of the platform (and therefore the heels) have been raised by an amount simulating the height of a shoe heel which is considered suitable for compensating the defect shown in FIG. 6.

When the geometric centres and the barycentres are substantially superimposed (which is equivalent to substantial flattening of the triangles until a transverse line is formed between the two feet), the height of the heel is optimum. The heel height thus obtained may be used to provide the patient with the appropriate corrective heels.

In other words, it is possible to perform firstly measurement of the foot-sole pressures in the completely flat condition of the footplate in order to determine the position of the overall barycentre and the barycentres of the individual feet and the position of the centres of the polygons for the overall contact pressure and that of the individual feet.

An optimum equilibrium is achieved when the barycentres, detected by the podometric pressure examination, coincide with the geometric centres of the polygon for the overall contact pressure and the contact pressure areas of the individual feet.

In the case where an imbalance is identified, the platform is raised and the detecting of the foot-sole pressures in the condition with the footplate raised to the height of the measurement of the personalized heel is repeated, and the position of the barycentres of the individual feet and the position of the overall barycentre and the position of the centres of the polygons for the contact pressure of the individual feet and the position of the centre of the polygon for the overall contact pressure are recalculated.

If the barycentres at this point coincide with the geometric centres of the polygon for the overall contact pressure and that for the contact pressure areas of the individual feet, the optimum height of the shoe heels to be used has been determined.

The system according to invention, if provided with groups of telecameras 17, 18, may also allow a further useful postural analysis.

This further postural analysis is based on the front and lateral images of the body of the patient standing on the footplate.

Based on the front video image of the patient, the operator is able to define a number of reference points on the screen image via the input means of the terminal (for example the mouse). These reference points may be advantageously:
- a line corresponding to vertical centre line passing through the pubis of the patient;
- markers corresponding to the position of the anterior superior iliac spines (ASIS);
- markers on the sides of each knee-cap.

Figure 8:
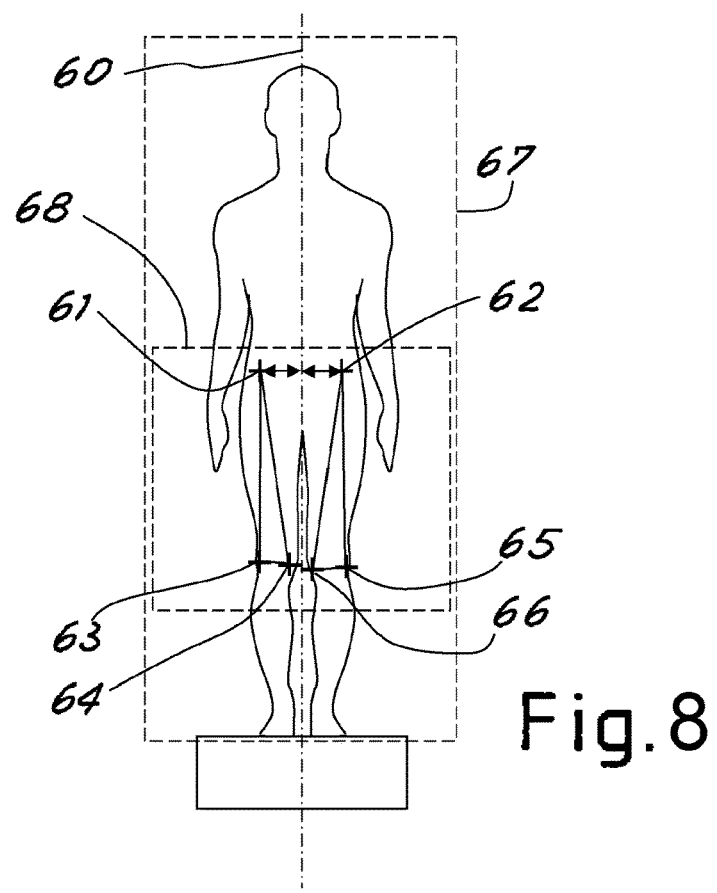
FIGS. 8 and 9 show respectively front and lateral schematic views of the system according to FIG. 1 during use.

FIG. 8 shows in schematic form these markers on a front profile of the body. The centre line is indicated by 60, the ASIS markers are indicated by 61, 62 and the side markers for the knee-caps are indicated by 63, 64 and 65, 66. The markers may be advantageously shown in the form of reference crosses.

The centre line may be advantageously positioned on the picture taken of the full body (detecting field indicated by 67), while the markers may be positioned with greater precision on the enlarged picture (detecting field indicated by 68). As already mentioned, the two detecting fields may be those of the two front telecameras or be obtained by a single telecamera which is operated so as to take various enlarged pictures.

Advantageously, after positioning these markers, the system may calculate and indicate on the video picture (using a method which per se may now be easily imagined by the person skilled in the art and therefore is not further shown or described here) the distances of the ASIS from the surface and the distance between the ASIS and the vertical centre line passing through the pubis, the side-to-side distance between the markers present adjacent to the knee-caps and the distance between the markers present adjacent to the knee-caps and corresponding ASIS. All of this is shown by way of example again in FIG. 8 and allows the identification, in the front plane, of any pelvic imbalance and the presence of inwards/outwards rotation of the knee-caps.

The vertical line helps assess more precisely the position of the various body segments, within the overall postural picture, relative to the vertical centre-line passing through the pubis.

Moreover, as can be seen in FIG. 8, the lines indicated between the markers of each ASIS and the associated knee-cap define a triangle for each leg. In the absence of anomalies (or after their correction by means of suitable raising of the rear part of the platform) the base (indicator of inwards rotation of the femur) and the height (indicator of apparent shortening of a limb) of the two triangles are substantially comparable for the two legs (as shown in FIG. 8).

Figure 9:
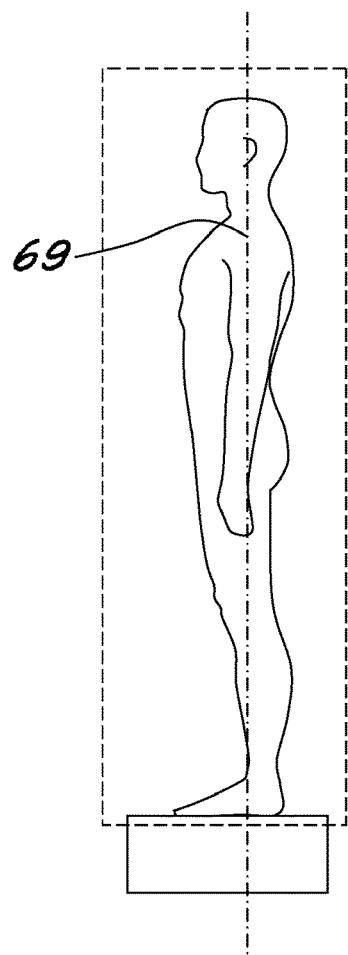

FIG. 9 show in schematic form a picture taken by the lateral telecamera. In this picture the operator is able to position (using the same methods mentioned above for the front picture) a vertical line 69 which passes through the lower ear lobe and allows better evaluation of the body posture in the space in relation to a line vertical to the ground in the sagittal plane.

In order to facilitate the positioning of lines and markers, the images recorded by the telecameras may if necessary be frozen by the operator (for example permanently saving the picture in an electronic memory of the control unit) so that it is possible to work on suitable static images.

A correct posture may be preferably defined by means of a complete analysis by the expert operator of the foot print and the front and lateral images as mentioned above.

Figure 10:
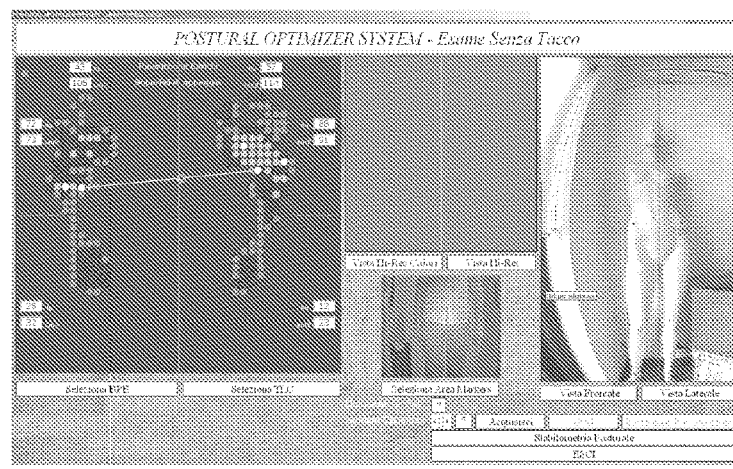
FIGS. 10 and 11 show further views of examples of graphical processing screenshots produced by the system according to FIG. 1.
Figure 11:
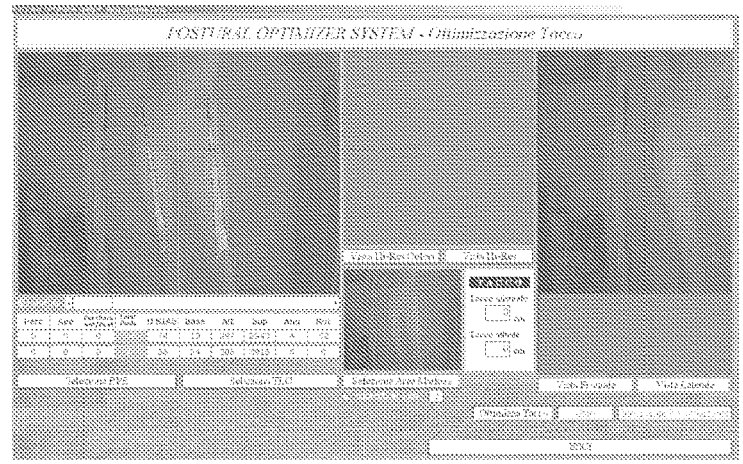

FIGS. 10 and 11 show examples of possible integrated screenshots which may be displayed by the terminal on the screen in order to provide the provide the operator with the appropriate information.

In particular, FIG. 10 shows a screenshot with, on the left, the processed image of the pressure zones detected on the platform 10, with, highlighted, the barycentres, the geometric centres and the percentage distribution values of the loads between the feet and the front and rear part of each foot. The same figure shows instead on the right-hand side the front image of the full body and in the centre the partial front picture (taken the front telecameras), on which the points and the axes already described above with reference to FIG. 8 are to be marked.

FIG. 11 shows, instead, a screenshot with various pictures taken by the telecameras and geometric data highlighted on them. In the left-hand picture it is possible to note the triangles marked by the system between the ASIS and sides of the knee-caps. The screenshot shows in the centre also the heel value set, namely the height of the rear part of the platform with respect to the horizontal for raising the heels of the foot.

Since the set of data detected by the system may be easily stored digitally by the terminal on a suitable medium (for example a hard disk), also in large quantities, it is possible to create a data archive for the various patients, and checks and comparisons of the data acquired may also be performed, as may be now easily imagined by the person skilled in the art.

Figure 15:
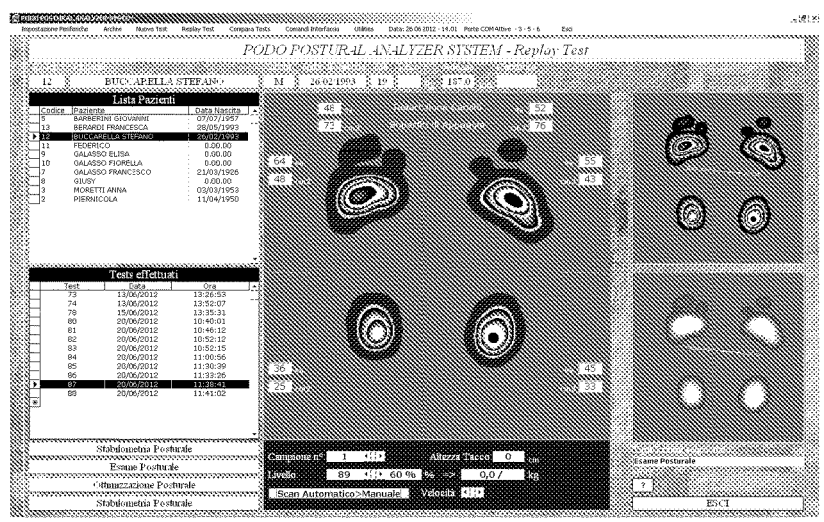
FIG. 15 shows a further possible graphical processing screenshot produced by the system according to FIG. 1.

For example, FIG. 15 shows a possible screenshot where, for a list of patients undergoing tests, the data detected and stored for each of them may be shown, also in graphic form. Several tests for each patient may thus be stored and ordered chronologically so as to have an overall picture of the improvement or deterioration in the condition of the patient over time.

At this point it will be clear to the person skilled in the art how the system according to the invention may be used to detect baropostural data.

The procedure for using the system may easily involve an initial objective examination, subsequent detecting by instruments, positioning of the markers, podometric video examination of the feet without shoes and podometric video examination of the feet with simulation of personalized shoe heels, verification and comparison of the data acquired.

The objective data may comprise the collection of personal details and the case history of the patient; the detecting, with the patient standing erect in the station with feet substantially together, in the front plane, of any pelvic imbalance and the presence of inward/outward rotation of the knee-caps; with forward flexing of the trunk by the patient it is possible to detect the presence of any real or apparent shortening of a lower limb; with the patient lying supine the freedom of the coxo-femoral joints in the transverse plane; with the patient lying prone with knee bent at 90° the postural abnormalities or dysmorphisms affecting the feet suspended in the space may be studied.

It is possible to carry out a podometric video examination of the feet without shoes, detecting the foot-sole pressure points in the completely flat condition of the footplate, in order to determine the position of the overall barycentre and barycentre of the individual feet and the position of the centres of the polygons for the overall contact pressure and the contact pressure of the individual feet.

Furthermore, based on the video detecting of the patient, it is possible to position the markers and the reference lines, detecting the spatial position of the ASIS, the distance of the ASIS measured from the surface and the distance between the ASIS and the vertical centre line passing through the pubis, the side-to-side distance between the markers present adjacent to the knee-caps, and the distance between the markers present adjacent to the knee-caps and the corresponding ASIS.

The front video detecting of the full body of the patient may be used to observe the position of the various body segments, within the overall postural picture, relative to the vertical centre-line passing through the pubis.

The front video detecting of the full body of the patient may be used to observe the position of the various body segments, in the sagittal plane, relative to the vertical centre-line passing through the base of the fifth metatarsus.

As mentioned above, the postural anti-gravity resistances, created by a locomotor apparatus in the space, determine uniform adaptation of the body load distribution on the foot-sole pressure points.

An optimum equilibrium is achieved when the barycentres, detected by means of the podometric pressure examination, substantially coincide with the geometric centres of the polygon for the overall contact pressure and the contact pressure areas of the individual feet.

The absence or the correction carried out of the postural anomalies is thus indicated graphically when:

a) in relation to the front plane, the base (indicator of inwards rotation of the femur) and the height (indicator of apparent shortening of a limb) of the two triangles (the vertices of which consist of the markers positioned on the side of each single knee-cap and on the corresponding ASIS) are comparable;

b) in relation to the plane of the pressure sensors, in the picture which shows the overall and partial barycentres of the feet and the geometric centres of the contact pressure areas, the surfaces of the two triangles (the vertices of which consist of the barycentres of the forces acting on the footplate and the centres of the contact pressure areas of the feet) are reduced, confirming that an optimum equilibrium has been reached.

Optimization of the height of the platform for effecting postural corrections may be carried out tentatively, based also on the experience of the operator, observing for each height set the correction detected by the system.

However, it is possible to have a prior indication of the height of a possible shoe heel (the correctness of which is then tested by the raising the footplate as mentioned above), by means of the patient assuming a prone lying position with the knee bent at 90°.

In this position the foot in fact assumes a natural position with the base of the metatarsal heads directed more or less upwards. The difference in height between the centre of the heel of the foot and the metatarsal heads has been found to provide a good indication of the heel height to be set on the platform and to be verified with the system according to the invention. This is shown schematically in FIG. 14.

This height difference may be detected using various systems, such as a mechanical measurement system or a 3D scanner.

However, advantageously, it may be measured using an accessory with which the system according to the invention may be equipped.

Figure 12:
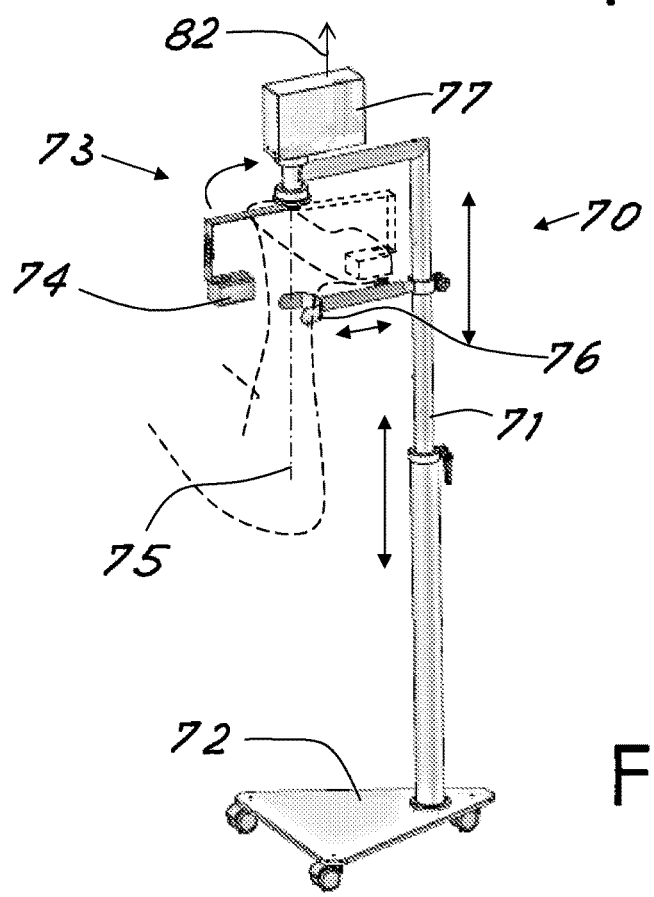
FIG. 12 shows a schematic perspective view of an accessory of the system according to FIG. 1.
Figure 13:
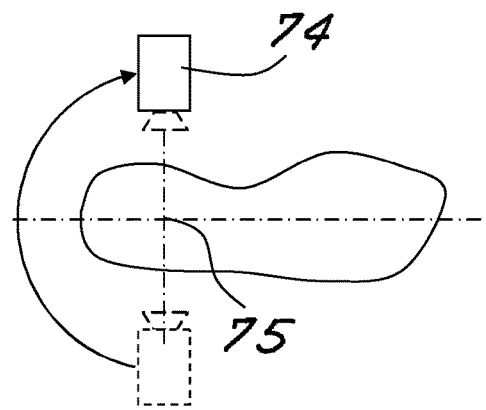
FIGS. 13 and 14 show respectively a top plan view and side elevation view, during use of the accessory according to FIG. 12.
Figure 14:
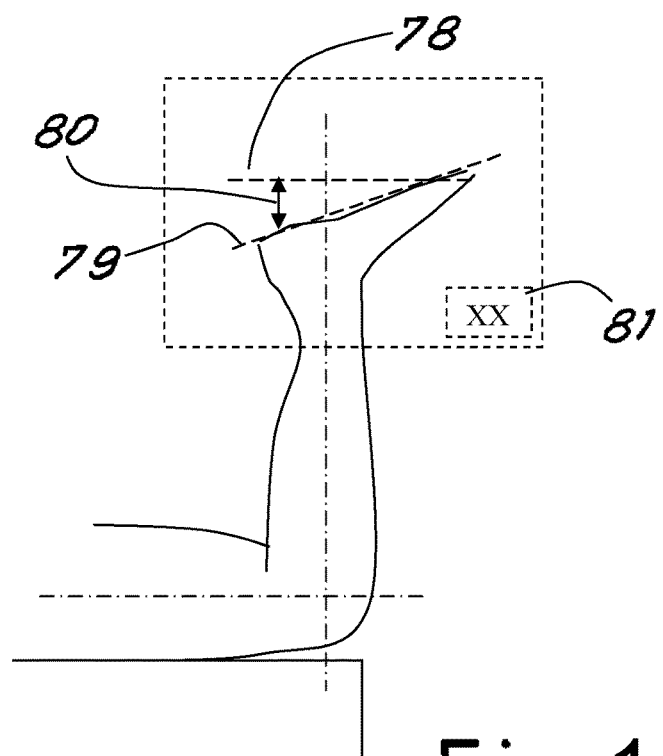

This accessory, which is generically denoted by 70, is for example shown in FIGS. 12, 13 and 14.

Advantageously, the accessory 70 comprises a support 71 which is adjustable heightwise, preferably with a base 72 resting on the ground and provided with roller wheels, and which carries a device 73 for taking a picture of a foot. For example, the device may comprise a telecamera 74 which has a substantially horizontal viewing direction and which is aimed at a detecting zone where the patient's foot is positioned in the said prone lying position with the knee bent at 90°, as shown by way of example in broken lines in FIG. 12.

A 3D scanner of the type substantially known per se for detecting the feet in three-dimensional form may also be used instead of a telecamera. The scanner may also be of the static type, namely without the need to rotate about the foot, for example because it comprises two or more 3D sensors arranged at a suitable angle around the foot.

In order to facilitate positioning of the foot with respect to the detecting device, the support 71 also has a centring carriage 76 intended to accommodate a tibial zone of the patient's leg. The heightwise adjustment of the support 71, for example by means of a telescopic mechanism in the support, and the vertical lockable sliding action of the component 76, allow correct heightwise positioning and centring of the device with respect to the side of the foot.

Advantageously, the device 73 also allows rotation of the detecting device, in particular if it comprises a telecamera, about a vertical axis 75, with the telecamera which, during rotation, has its viewing direction which remains substantially horizontal and which is aimed at the axis 75. Rotation of the device about the axis 75 may be advantageously performed by means of an actuator or gearmotor 77.

Preferably, the detecting device rotates about the foot from one side to the other, passing behind the rear of the foot, as shown schematically in FIG. 13, so as to have an overall view of the arrangement and form of, the foot.

The accessory 70 is advantageously connected to the control unit 12 so as to provide the operator with a lateral screenshot of the foot, similar to that shown schematically in the box indicated by broken lines in FIG. 14. In particular, the telecamera may be connected to the acquisition means 30 (or equivalent acquisition means). The connection between the accessory and the control unit may be advantageously of the wireless type (for example standard WIFI for data transmission on a local network), as schematically indicated by 82 in FIG. 12.

The rotational movement of the telecamera or the scanner may controlled so as to obtain the desired side view of the foot and, if necessary, also the rear view and view from the other side of the foot. Moreover the continuous movement may provide an overall view of the foot to be stored in the system for future use. Operation of the rotational actuator 77, where present, may be performed by the said control unit 12.

Once the lateral image has been acquired and shown on the screen (where necessary, "frozen"), the operator may position on the image two reference lines 78 and 79 by means of the input systems of the terminal (for example mouse). As can be clearly seen in FIG. 14, the line 78 is a horizontal line which is positioned so as to pass adjacent to the metatarsal heads of the foot, while the line 79 is a line which is positioned so as to pass along the sole of the foot, adjacent to the metatarsal heads of the foot and contact surface of the heel. By positioning on the screen a measurement line 80 which passes vertically through the centre of the heel, the measurement of the possible heel height to be set on the platform and to be checked with the system according to the invention, as mentioned above, is displayed on the screen at 81.

At this point it is clear how the predefined objects have been achieved. With the system and the method according to the invention a plurality of baropostural information may be easily obtained and, advantageously, the useful heel height for correcting any postural defects may be verified.

In particular, it is possible to obtain angular and linear measurements of the feet in the space, outside of the body load, useful for examining the morphology of the feet; the analysis of the distribution of the body weight of a patient standing in the erect station on the foot soles; the qualitative analysis of the extent of any dysmorphism affecting the feet, the lower limbs, the pelvis and the entire locomotor apparatus in the front plane; analysis of the posture of the body in the space in relation to a line vertical to the ground in the sagittal plane; the correction of any postural abnormalities or dysmorphisms measured by means of the simulated application of shoe heels with, the same personalized height; verification of the postural antigravity optimization acquired by means of the comparative study of the data without heels and with simulated heels.

It should be noted that, in order to optimize the posture, it has been found that advantageously a suitable heel height which is the same for both legs may be used. For this reason the platform according to the invention advantageously uses a single movable part common for both feet.

Obviously the description provided above of an embodiment applying the innovative principles of the present invention is provided by way of example of these innovative principles and must therefore not be regarded as limiting the scope of the rights claimed herein. For example, if required for particular applications, a raisable platform for each foot may be used, as may be now easily imagined by the person skilled in the art.

The invention claimed is:

1. System for detecting and displaying baropostural parameters, comprising:
 a platform with a footplate intended to accommodate a person standing on it and provided with sensors for detecting pressure distribution of the imprint of the two feet on the footplate;
 an electronic acquisition device connected to the sensors for digital acquisition of the pressure distribution in order to create a map of the pressure points of the feet on the footplate;
 calculation means designed to calculate, for each foot and for both feet on the footplate, the geometric centres and the barycentres of the map of the pressure points; and
 display means which display on a screen a graphical representation of the imprints of the two feet on the footplate together with the corresponding geometric centres and barycentres calculated by the calculation means.

2. The system according to claim 1, characterized in that the footplate has at least one rear zone for resting the heels, which can be controllably raised.

3. The system according to claim 1, characterized in that the raisable rear zone is hinged together with a front part of the footplate so as to tilt and rotate about an axis transverse to the feet by means of a motorized actuator.

4. The system according to claim 1, characterized in that the display means display on the screen for each foot a triangle with the three vertices situated, respectively, in the geometric centre and in the barycentre calculated for that foot and in the overall geometric centre calculated for the two feet.

5. The system according to claim 1, characterized in that it comprises a front telecamera group and/or lateral telecamera group for detecting front and/or lateral images of a person standing on the footplate and controllably displaying the images on the screen by means of image acquisition means.

6. The system according to claim 5, characterized in that the footplate is situated on the top side of a base from which adjustable supports project for supporting the telecamera groups in the respective front and side positions relative to the base.

7. The system according to claim 5, characterized in that it comprises input means for the user which receive commands from the user for controlling the display means so as to display on a front image on the screen three markers for each leg arranged in pairs on the sides of the knee-cap and one marker on the corresponding anterior superior iliac spine, the display means also displaying a pair of triangles, each of which with the three vertices situated respectively on said three markers for each leg.

8. The system according to claim 5, characterized in that it comprises input means for the user which receive commands from the user for controlling the display means so as to display on a front image and/or a side image of the person a corresponding vertical postural reference line.

9. The system according to claim 1, characterized in that it comprises an accessory for measuring the difference in height between the metatarsal heads and the heel of a foot when the person is lying in a prone position with the knee hem at 90°.

10. The system according to claim 9, characterized in that the accessory comprises: a detecting device for detecting the foot at least laterally, which sends the image to image acquisition means for displaying it on a screen by means of display means;
 input means for the user which receive commands from the user for controlling the display means so as to display on the lateral image of the foot a first horizontal line passing adjacent to the metatarsal heads and a second line passing along the metatarsal heads and the heel, and the calculation and display means being designed to calculate and display on the screen a measurement of the vertical distance between said first and second line in the zone of the heel.

11. The system according to claim 10, characterized in that the detecting device comprises a telecamera supported so as to rotate about a vertical axis situated in the detecting field thereof, so as to be able to rotate at least partially about the foot to be recorded and arranged close to this vertical axis.

12. Method for detecting and displaying baropostural parameters by means of an electronic system, comprising the steps of:
   acquiring electronically the pressure distribution of the imprint of the two feet of a person standing on a footplate with a pressure-sensitive surface;
   creating a map of the pressure distribution acquired;
   calculating, for each foot and for both feet on the footplate, the geometric centres and the barycentres of the map of the pressure points;
   displaying on a screen a graphical representation of the imprints of the two feet together with the corresponding geometric centres and barycentres calculated.

13. The method according to claim 12, wherein, before a step for acquiring the pressure distribution of the imprint of the two feet of a person, the pressure-sensitive surface is controllably raised by a predetermined amount in the heel contact zone.

14. The method according to claim 13, wherein the predetermined amount depends on the difference in height between the metatarsal heads and the heel of a foot when the person is in the position lying prone with the knee bent at 90°.

15. The method according to claim 12, wherein a triangle with the three vertices arranged respectively in the geometric centre and in the barycentre calculated for that foot and in the total geometric centre calculated for the two feet is calculated and displayed on the screen for each foot as an image representing the quality of the posture.

16. The method according to claim 13, wherein the amount of the raising movement is set so as to reduce the distance between geometric centres and corresponding barycentres calculated on the pressure distribution map.

17. The method according to claim 12, wherein the pressure distribution map is displayed on the screen as an image, representing the imprints of the feet, with zones having different colours depending on die pressures detected.

18. The method according to claim 12, in which front images of the person standing on the footplate are recorded, the images are displayed on a screen and three points, two of which corresponding to the sides of the knee-cap and one point corresponding to the associated anterior superior iliac spine, are indicated on them for each leg, and two triangles, each with the three vertices arranged respectively on said three points for each leg, are displayed on the screen as postural indicators.

* * * * *